United States Patent
Labrecque et al.

(10) Patent No.: US 12,219,934 B2
(45) Date of Patent: Feb. 11, 2025

(54) DETECTING ESTRUS IN ANIMALS FOR INSEMINATION

(71) Applicant: Groupe Ro-Main Inc., Saint-Lambert-de-Lauzon (CA)

(72) Inventors: Jacquelin Labrecque, Saint-Lambert-de-Lauzon (CA); Gabrielle Germain, Saint-Narcisse-de-Beaurivage (CA); Eva Bourgeais-Boon, Levis (CA); Joel Rivest, Levis (CA)

(73) Assignee: Groupe Ro-Main Inc., Saint-Lambert-de-Lauzon (CA)

( * ) Notice: Subject to any disclaimer, the term of this patent is extended or adjusted under 35 U.S.C. 154(b) by 111 days.

(21) Appl. No.: 17/819,759

(22) Filed: Aug. 15, 2022

(65) Prior Publication Data

US 2023/0057738 A1   Feb. 23, 2023

Related U.S. Application Data

(60) Provisional application No. 63/235,266, filed on Aug. 20, 2021, provisional application No. 63/235,270, filed on Aug. 20, 2021.

(51) Int. Cl.
*A01K 29/00* (2006.01)
*A61B 5/00* (2006.01)

(52) U.S. Cl.
CPC ......... *A01K 29/005* (2013.01); *A61B 5/0077* (2013.01); *A61B 5/4368* (2013.01); *A61B 2503/40* (2013.01)

(58) Field of Classification Search
CPC . A61B 5/0077; A61B 5/4368; A61B 2576/00; A61B 2503/40; A01K 29/005
See application file for complete search history.

(56) References Cited

U.S. PATENT DOCUMENTS

| 6,925,965 B1 | 8/2005 | Hurwitz | |
| 2003/0069515 A1* | 4/2003 | Theelen | A61D 17/002 600/551 |
| 2020/0125849 A1* | 4/2020 | Labrecque | H04N 23/54 |

FOREIGN PATENT DOCUMENTS

| CN | 110839557 | | 2/2020 | |
| CN | 110839557 A | * | 2/2020 | ........... A01K 29/005 |
| CN | 110991222 A | * | 4/2020 | ............. G06F 18/22 |
| CN | 111467074 | | 7/2020 | |
| EP | 1900278 | | 3/2008 | |

(Continued)

*Primary Examiner* — Boniface N Nganga
(74) *Attorney, Agent, or Firm* — Adrian D. Battison; Ade & Company Inc.; Ryan W. Dupuis (57) ABSTRACT

A method for detecting estrus in sows where insemination is carried out when a determination has been made. In a first method images of a rear profile of each sow are analyzed to make a determination from features relating to a shape, size, and/or color of the vulva whether the sow is in estrus. The analysis can use a program where a large number of images showing the vulva area of a plurality of sows known to be in estrus and known not to be in estrus have been previously analyzed to generate data on the previous images to create a program which generates a signal using the data to make the determination. In a second method a boar is confined and brought into close contact with the sows where images and/or sounds of each sow are analyzed to make a determination whether the sow is in estrus.

16 Claims, 6 Drawing Sheets

(56) References Cited

FOREIGN PATENT DOCUMENTS

| | | | |
|---|---|---|---|
| EP | 1300119 | | 4/2009 |
| TW | I785729 B | * | 12/2022 |
| WO | WO 2007006579 | | 1/2007 |
| WO | WO 2010/010006 | | 1/2010 |
| WO | WO 2014083433 | | 6/2014 |

* cited by examiner

DETECTING ESTRUS IN ANIMALS FOR INSEMINATION

This application claims the benefit under 35 USC 119 (e) of Provisional applications 63/235,266 and 63/235,270 both filed Aug. 20 2021.

This invention relates to a method for detecting estrus in animals for use in insemination.

BACKGROUND OF THE INVENTION

For efficient animal husbandry, a lot of attention has been given to looking for effective methods to determine when the animal concerned is in estrus so that an insemination can be carried out with better probability of success.

It is known that changes in movement and demeanor can be used to detect estrus including changes in ratio of standing to lying periods. Also temperature of the body or particularly the vaginal area can be used to make a determination.

However further improvements in techniques to make a determination are required.

The present invention is particularly applicable to sows where the worker typically has less contact with the animals thus requiring a more automated method which can provide the determination for estrus. However the method can be used on other animals.

SUMMARY OF THE INVENTION it is an object of the present invention to provide a method of raising livestock comprising:

defining a confinement area in which a group of sows are contained, where the sows are potentially in estrus;

providing a boar which is confined or contained;

the confinement area and the container being arranged so that the sows in the containment area are enabled to come into close contact with the boar by movement of the boar or the sow;

providing at least one collecting device arranged to collect images and/or sounds of each sow when in said close contact;

and analyzing using a control system the images and/or the sounds to make a determination whether the sow is in estrus for insemination.

The method herein can thus use either images from a camera or can use the sounds generated by the sow or can combine analysis of both sets of data, when the sow is in close contact with the boar.

In the preferred method, the images are taken from a front of the sow to show the body and head since these are indicative of the changes of movement and demeanor which are determinative of estrus. In particular, the images of the front elevation of the sow can be taken from the front when the sow is in close proximity to the front of the boar where it is expected that the changes will be most apparent.

In the preferred method, the images are analyzed for movements of the sow characteristic of estrus which have been determined by previous analysis of sows known to be in estrus and making a comparison with the currently obtained image or images. Multiple comparisons can be made to obtain more accurate results using statistical analysis to discard errors.

In particular the images can be analyzed looking for characteristics known to be indicative of estrus including:
speed of movements characteristic of estrus.
movements of the body characteristic of estrus.
movements of the head characteristic of estrus.
movements of the ears characteristic of estrus.
angular velocity of the ears characteristic of estrus.
movements of the dorsal area characteristic of estrus.
changes in posture of the body characteristic of estrus.

In particular the sounds can be analyzed looking for characteristics known to be indicative of estrus including:
specific types of sounds created by the sow characteristic of estrus, such as squealing, grunting.
a spectrum of frequencies characteristic of estrus.
a sequence of sounds characteristic of estrus.

Preferably the collecting device comprises a camera which is mounted on an apparatus for containing or confining the boar and directed toward the sow at the apparatus.

In one embodiment the apparatus for containing or confining comprises a structure which is movable and the boar is taken to the sows while the sows are in individual containment pens. This is typically a boar cart where the boar is contained within a cage and moved on a supporting floor along alleyways to the sows contained in crates along the alleyway. The boar cart provides the best way to contain and control the large boar as it is moved from sow to sow. However other means for transporting the boar can be used for example a simple tether or a guidance robot device to which the boar is tethered while it walks from sow to sow.

In an alternative arrangement, the apparatus for containing or confining the boar is fixed in place as a fixed cage within an open confinement area where the sows are free to move from place to place including up to the boar which is separately confined within its own cage within the confinement area.

In both cases the camera is preferably located on the cart or on the cage facing the sow to be imaged so that a series of images of the sow can be obtained as it approaches or is approached to use those images in analysis of the movements of the sow as defined above.

Preferably the microphone is also located on the boar cage and is of a type which is directional to receive primarily sounds from the sow at the boar container.

While the above statements use the term "boar", it is appreciated that this can be an actual live animal. However, the boar can be a fabricated structure which provides one or more stimuli to the sow which simulate a live animal. In an extreme case, the "boar' could simply be the use of a pheromone spray to sufficiently simulate the boar. It has been found that the live animal is more effective in stimulating the sow for detecting estrus and for accepting the insemination. However improvements in simulation stimuli may avoid the necessity for transporting or caging an actual live and very large animal.

In an important optional feature, which can be used with any of the above statements or with any of the features defined hereinafter, the control system operates to distinguish between determinations of estrus requiring simple and complex analyses where in simple analyses, an output signal is provided indicative of a determination of estrus in the sow and where in complex analyses an output signal is provided requiring additional intervention before a determination of estrus is made. That is the system can generate and indicate a level of confidence in the result which allows the system to move directly to a determination or to indicate that confidence is low requiring further data to be supplied. For example, further data may come from the methods described below or from other intervention by a worker. As another example, a worker may be employed to apply pressure to the dorsal area of the sow during the collection of sounds and/or images.

The outcome of the determination is that an insemination is carried out on receipt of a signal indicative that the final determination has been made so that the probability of success of the insemination procedure is increased.

In another method which can be used herein as a separate system or as part of the above analysis there is provided a method for raising livestock comprising:
  defining a confinement area in which a group of sows are contained, where the sows are potentially in estrus;
  periodically collecting images of a rear profile of each sow;
  analyzing each image to determine an area on the image showing the vulva of the sow;
  and analyzing, using a control system, the images of the area to make a determination from features relating to a shape, size, and/or color of the vulva whether the sow is in estrus;
  providing an output signal in response to a determination that the sow is in estrus;
  wherein insemination can be carried out on receipt of the signal indicative that a determination has been made.

The determination as to whether the sow is in estrus can be used for timing insemination or to simply know that the animal came into heat. In some cases there are sows for which the farmer wants to skip an estrus cycle to optimize reproductive results;

In a preferred method, the analysis is carried out by the control system using a program where a large number of images showing the vulva area of a plurality of sows known to be in estrus and known not to be in estrus have been previously analyzed to generate data on the previous images to create a program which generates a signal using the data to make the determination. Thus the program operating the control system is a neural network which has pre-learned the characters to determine the presence of estrus by analyzing large numbers of images of the vulva area of animals which are known to be in estrus and known to be not in estrus. This pre-learning programing can be stored in the control unit, which can be on-premise or on the cloud, to be applied to the new images to be analyzed.

While the above machine learning is carried out by the system itself, the present applicants have by extensive analysis of images found that a determination can be made based for example on a number of visual features which can be extracted from the image. These features can include one or more of the following:
  -a- texture of or wrinkles on the vulva; this relates to a degree of swelling of the area since the absence of wrinkles arises due to an increase in volume caused by blood engorgement which stretches the skin to reduce the depth and presentation of wrinkles.
  -b- height or width of the vulva; again this relates to a degree of swelling of the area since height and width of the area is increased by swelling.
  -c- color of the vulva; the presence of engorging blood acts to deepen the red color which can be observed.
  -d- outward protuberance of the vulva. Again, engorgement of the area by increased blood supply will act to expand the vulva in the direction outward of the body to generate an increased 3D effect which can be observed even from a 2D image when taken or selected at a suitable angle.

In some cases, particularly with older animals who have produced a number of litters, the vulva area may have less obvious changes so that an analysis of a single image may not be determinative. In this case a comparison with previous images from the same animal can be used to observe changes over time where at least one image of the area is compared to previous images of the area of the same sow to use differences over time to make the determination. That is in many sows, the changes are sufficiently clear that the presence of estrus can be detected from a single image or from a series of images taken at the same time so representative of a current status at the time of the test. It will be appreciated that images and the determinations therefrom are carried out repeatedly over a time period, for example daily, in order to determine as soon as the estrus has started. Thus a series of images are available over the time period for comparison. In other cases, the comparison with the older images is necessary to make the determination. However of course this requires that the images be associated with an identification of the animal concerned, which is simple to do if the animal is confined but requires additional action if the animal is free to move amongst others.

In a first step of the analysis, preferably multiple images of the rear profile are obtained and analyzed to select one or more suitable images best showing the area. Where the camera is mounted and arranged so that the angle and location relative to the rear of the animal can change, many of the images of the rear profile may be unsuitable to show the vulva area so that the control system uses a program to select from the images those that are suitable and to use those in the determination. As part of this analysis, it is necessary for the system to select from the whole image of the rear profile the relevant vulva area so that a part of the algorithm requires that this area be first determined and selected onto an image component for the further analysis to take place. That is, after the vulva areas have been selected, it is then necessary to select from that subset of image components those that best show the area and should be used in the determination. Each image is then assessed by the system to determine whether it indicates a positive or negative result. Following that determination, a comparison of all positive and negative results will lead to a final determination and a confidence level indicated by how many of the results are in agreement. This information can be made available for an assessment whether insemination should occur, that is whether the vulva shows signs of estrus, or whether a further analysis with further data is required.

After the first analysis to select from the rear profile images a number in the subset which best or suitable show the vulva area, these multiple images of the area are selected and compared to obtain the determination using statistical analysis.

In some embodiments, the sows are confined in individual stalls and the images are obtained by a camera mounted on the stall. In this case the camera can be mounted in a fixed location on the stall and be timed and triggered to take images of the rear profile repeatedly at a frequency, for example daily, determined by the system. The camera can then take multiple images of the rear profile for the above analysis. This takes into account that the animal may not be in a suitable position or at a suitable angle relative to the camera for the best rear profile images to be obtained. In other cases, images are taken by a moving camera (on a rail, robot, etc.) so that these also may not all be suitable.

Preferably the images of the rear profile are taken while the animal is standing as this ensures that the vulva area is properly presented in a rearward direction and locates the vulva area in a particular location in the image which allows it to be more easily selected. Also this standing position ensures that the parts of the area are presented in the image in a consistent manner allowing a more effective analysis.

It may be desirable therefore to ensure that the animal is standing when the images are acquired or even to cause the animal, by some form of physical stimulation, to move to the standing position for the images to be obtained.

In some embodiments, the sows are unconfined in individual stalls so that they are free to move around. In this case, the images can be obtained by a camera mounted at a suitable location such as on a feeder or water stall which are frequently visited by the sows. This could also be at a boar exposure station where there is an opening for sow to see the boar to get sexual stimulation. In this way each sow moves to the camera at random times and can be imaged each time it moves to the location concerned. In one arrangement, is necessary in this situation to apply an ID to the animal being imaged so that the animal can be identified for insemination. Thus in this case, the animals may be tagged using a readable tag such as an RFID ear tag. This ID can also be used for the historical comparisons above.

As an alternative, where ID information is not available, after a determination a mark can be applied to a sow which is the subject of the determination for subsequent insemination. Such marking systems by a paint spray or dabber are available and can be activated to mark the sow concerned. This is particularly effective where the imaging camera is located on a feeder stall which has walls confining one animal at a time so that single animal can enter, can be confined in a suitable orientation for imaging, imaged and the determination made before the animal is released back to the population. As an alternative, an alley may be provided between two zones such as a rest zone and a feeding zone where the animal is temporarily held for the actions to be competed before continuing to the next zone.

In some cases, the system may be provided as a program which can be applied to an existing imaging system such as a mobile phone. In this case, the images can be taken manually by a worker holding the imaging device with the worked providing information on the animal concerned for data storage and selecting the images to be taken. From those images, the control system takes over and selects the area images to be used and from multiple images makes the determination to be communicated to the worker. In other cases, the control system can be part of standalone system including a camera, a processor for making the determination and an interface for communication with a worker. In both cases the control system can be arranged to provide data relating to the determinations for a plurality of sows to a sow management system.

As explained in detail above, the method using the images can be used in conjunction with providing a boar which is confined or contained where the confinement area for the sows and the confinement system of the boar are arranged so that the sows in the containment area are enabled to come into close contact with the boar by movement of the boar or the sows.

BRIEF DESCRIPTION OF THE DRAWINGS

One embodiment of the invention will now be described in conjunction with the accompanying drawings in which.

DETAILED DESCRIPTION

Figure 1:
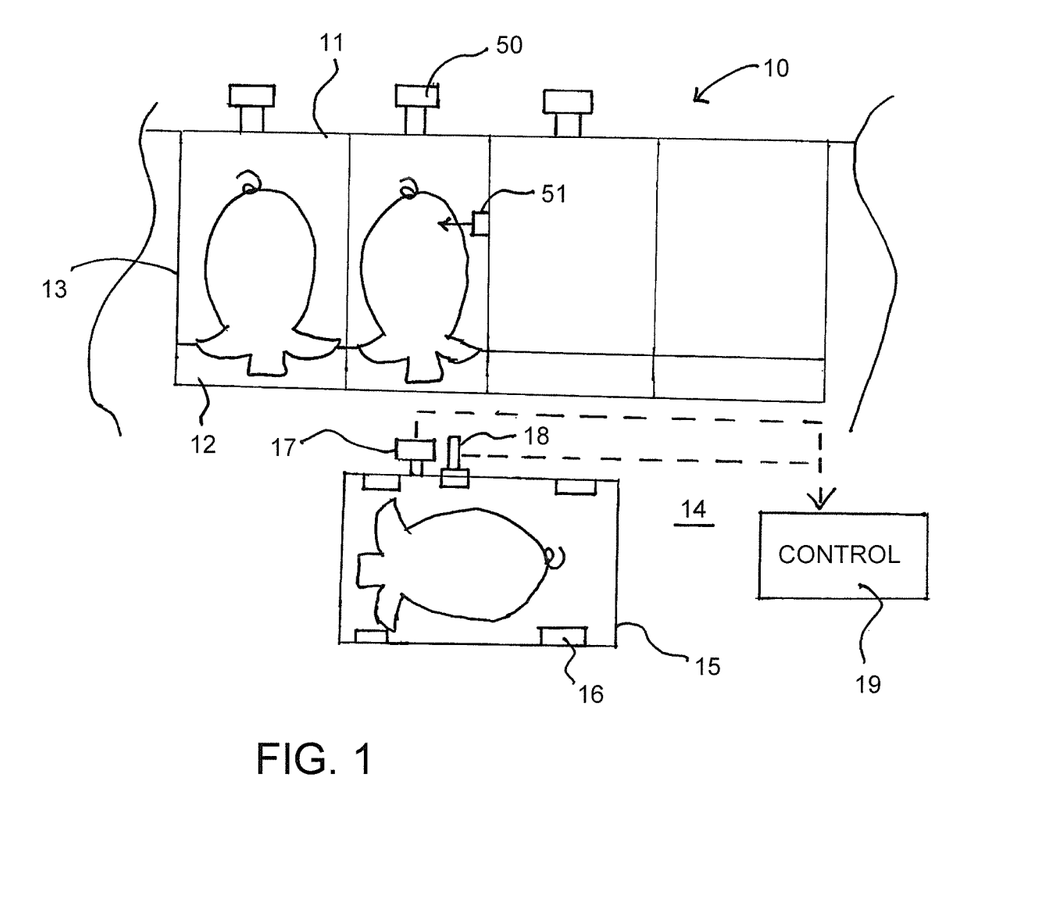
FIG. 1 is a schematic plan view of an animal husbandry barn showing the arrangements used in a first embodiment of a method according to the present invention.

In FIG. 1 is shown the components used in the method of raising livestock. A confinement area 10 includes a plurality of side-by-side breeding pens 11 for confined sows arranged in a row along an alley 14.

The pens are formed by pen walls of welded bars with a feed trough 12 along a front wall so that the animals remain confined during the breeding period in which a group of sows are contained, where the sows are potentially in estrus.

A boar is contained in a movable boar cart 15 on wheels 16 so is movable along the alley 14 to be brought up to each sow in turn and enabled to come into close contact with the boar by movement of the boar. A suitable cart is shown in prior U.S. Pat. No. 6,196,975 (Labrecque) issued Mar. 6 2001 and U.S. Pat. No. 6,508,202 (Kleinsasser) issued Jan. 21 2003 and both assigned to the present applicant, the disclosures of which are incorporated herein by reference.

The cart carries a camera 17 and a microphone 18 at fixed position on the cart so that the camera takes images and the microphone collects sounds of each sow at the time when in said close contact. Thus the camera and microphone are located on the frame of the cart at a suitable location to be directed at the required position when the cart is in registry with the sow pen.

The images and the sounds are communicated by wire or wireless to a control system 19 which analyzes the data as set out below to make a determination whether the sow is in estrus for insemination.

Figure 3:
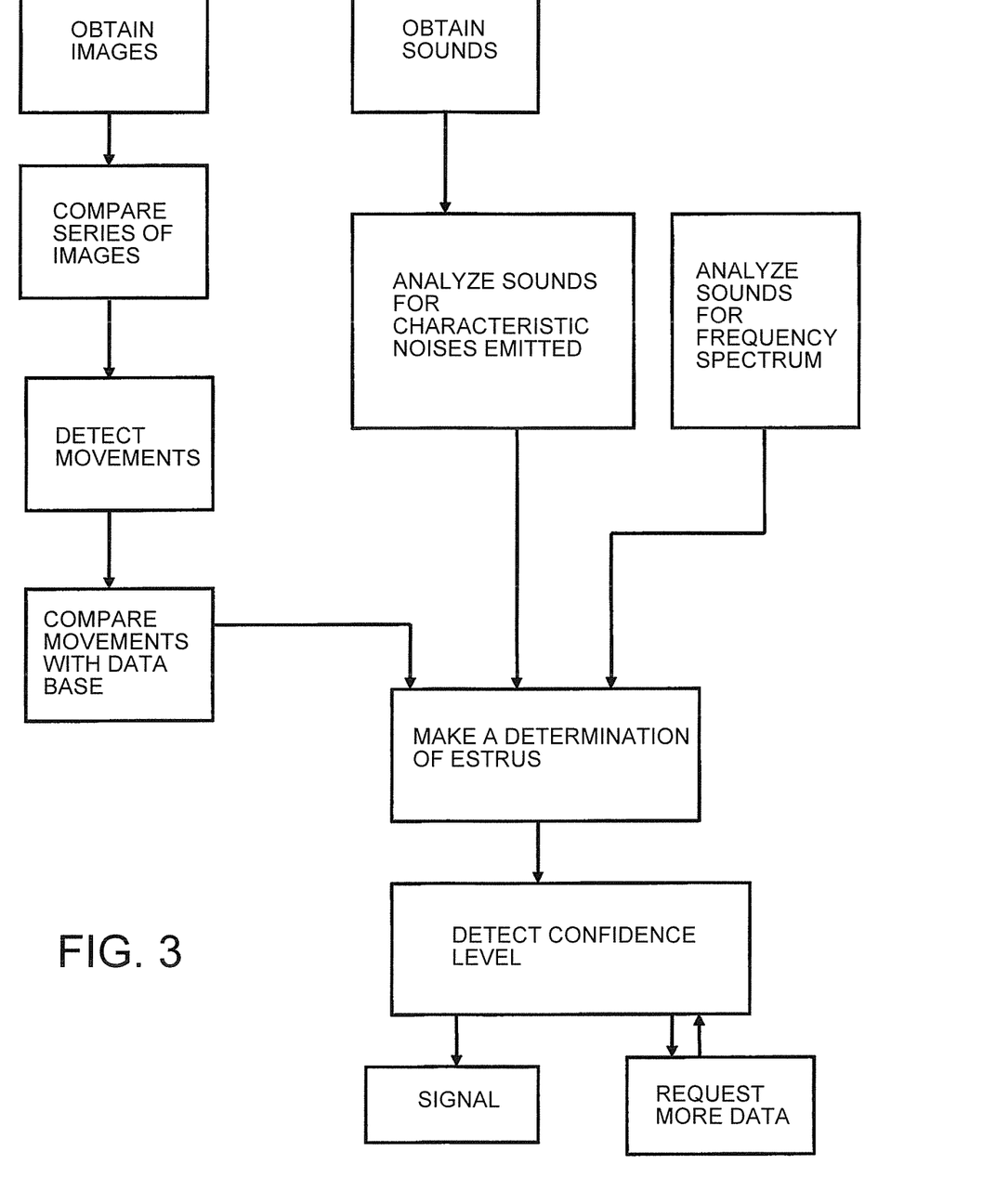
FIG. 3 is a flow chart showing the steps of a first embodiment of a method according to the present invention.

As shown in the flow chart of FIG. 3, the method uses either images from a camera or the sounds generated by the sow or can combine analysis of both sets of data where the images and sounds are taken when the sow is in close contact with the boar. The steps of the method are shown in detail in FIG. 3.

In the preferred method, the images are taken from a front of the sow as a front elevation to show the body and head since these are indicative of the changes of movement and demeanor which are determinative of estrus. In particular, the images of the front elevation of the sow can be taken from the front when the sow is in close proximity to the front of the boar where it is expected that the changes will be most apparent.

As shown in FIG. 3, the images are analyzed for movements of the sow characteristic of estrus which have been determined by previous analysis of sows known to be in estrus and making a comparison with the currently obtained image or images with the material from a data base. Multiple comparisons can be made to obtain more accurate results using statistical analysis to discard errors.

In particular the images can be analyzed looking for characteristics known to be indicative of estrus including:
speed of movements characteristic of estrus.
movements of the body characteristic of estrus.
movements of the head characteristic of estrus.

movements of the ears characteristic of estrus.
angular velocity of the ears characteristic of estrus.
movements of the dorsal area characteristic of estrus.
changes in posture of the body characteristic of estrus.

In particular the sounds can be analyzed looking for characteristics known to be indicative of estrus including:
specific types of sounds created by the sow characteristic of estrus, such as squealing, grunting.
a spectrum of frequencies characteristic of estrus.
a sequence of sounds characteristic of estrus.

Figure 2:
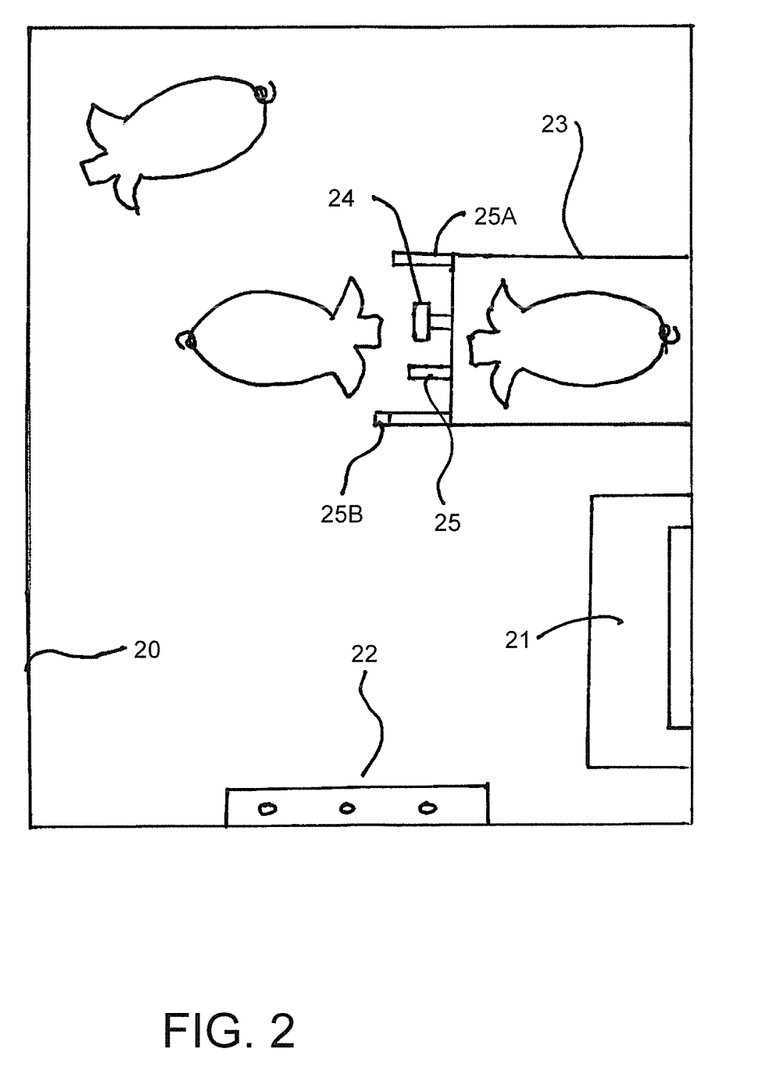
FIG. 2 is a schematic plan view of an animal husbandry barn showing the arrangements used in a second embodiment of a method according to the present invention.

As shown in FIG. 2, the sows are free within a confinement pen 20 for movement as they wish to a feeder 21, water supply 22 or to a rest area. A containment cage 23 for the boar is fixed in place as a fixed cage within the open confinement area where the sows are free to move from place to place including up to the boar which is separately confined within its own cage within the confinement area. In this case the camera 24 and the microphone 25 are located on the cage at a position to face the sow as it approaches the boar cage from the front of the boar. In this way a series of images of the sow can be obtained as it approaches to use those images in analysis of the movements of the sow as set out in FIG. 3. In FIG. 2, short dividing walls 25A and 25B are provided extending forward from the boar cage on each side of the sow when standing in front of the boar so that signals from only one animal are obtained and analyzed separately from other animals in the same general area.

The microphone 25 is an elongate directional microphone to receive primarily sounds from the sow directly at the boar container and to discard sounds from other areas of the containment area such as the other sows.

As shown in FIG. 3, the control system operates to distinguish between determinations of estrus requiring simple and complex analyses where in simple analyses, an output signal is provided indicative of a determination of estrus in the sow and where in complex analyses an output signal is provided requiring additional intervention before a determination of estrus is made. That is the system can generate and indicate a level of confidence in the result which allows the system to move directly to a determination or to indicate that confidence is low requiring further data to be supplied. For example, further data may come in response to the request from the methods described below or from other intervention by a worker. As another example, a worker may be employed to apply pressure to the dorsal area of the sow during the collection of sounds and/or images.

The outcome of the determination is that an insemination is carried out on receipt of a signal indicative that the final determination has been made so that the probability of success of the insemination procedure is increased.

In another method as shown in FIGS. 4 to 7, there is provided confinement area 30 in which a group of sows are contained, where the sows are potentially in estrus. The confinement area 30 includes separate pens 31 and 32 where the sow can enter to take feed from a trough 33 or from a water supply 34. The pens are typically arranged so that the sow can enter alone and other sows are excluded from entering at the rear of the pen. Each pen carries a fixed camera 35 which is operated to periodically collect images of a rear profile of each sow as that sow enters within the pen. As all sows will periodically take food, all of the sows will be the subject of the imaging system during their day. In this way each sow moves to the camera 35 at random times and can be imaged each time it moves to the location concerned. In one arrangement, is necessary in this situation to apply an ID to the animal being imaged so that the animal can be identified for insemination. Thus in this case, the animals may be tagged using a readable tag such as an RFID ear tag detected by a tag reader 37 at the pen 31.

Figure 7:
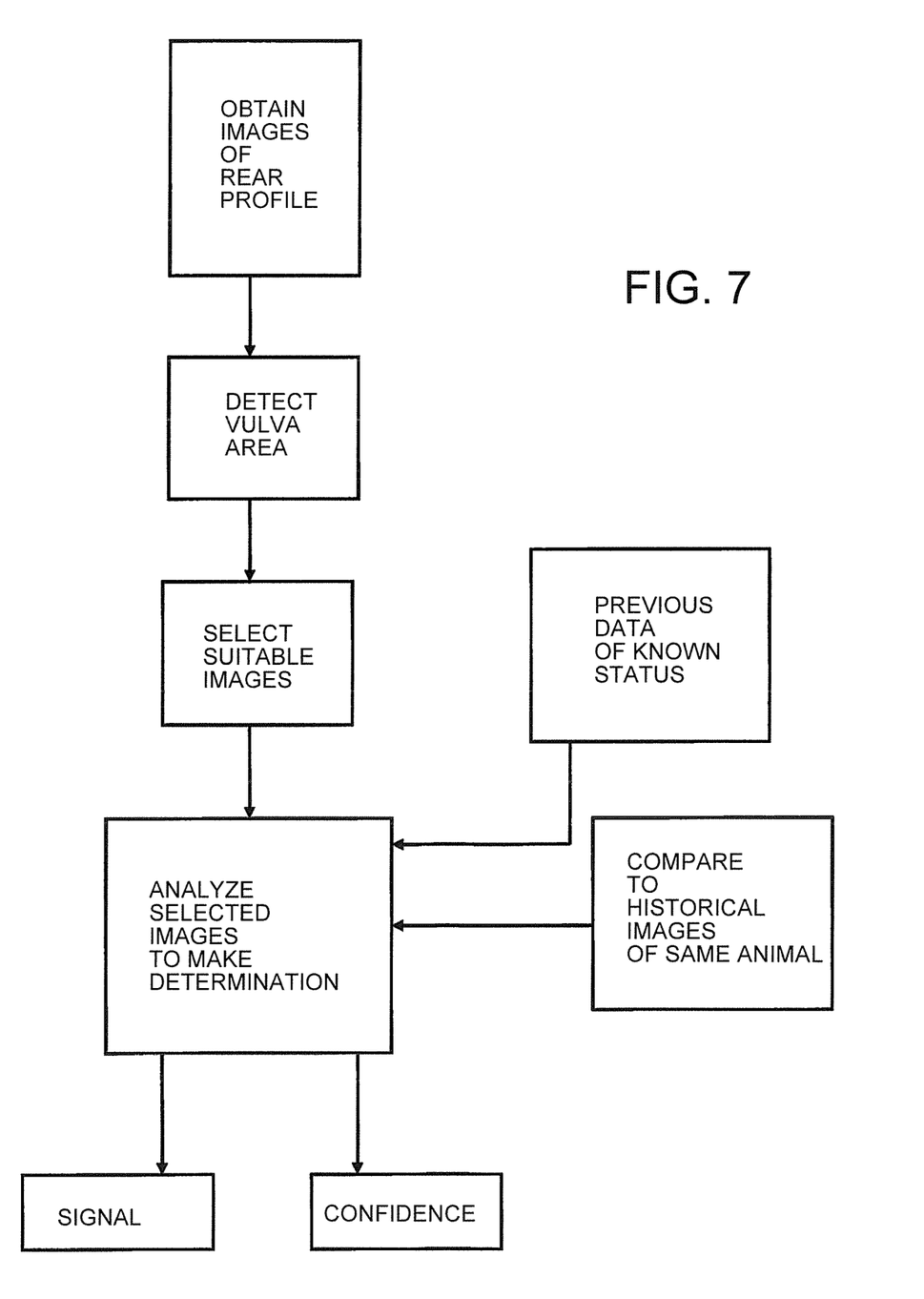
FIG. 7 is a flow chart showing the steps of the third embodiment of a method according to the present invention.

As shown in the flow chart of FIG. 7 where the steps are shown in detail, the control system receives the signals from the cameras and goes through a series of steps as shown for analyzing the mages to make a determination of estrus.

Figure 5:
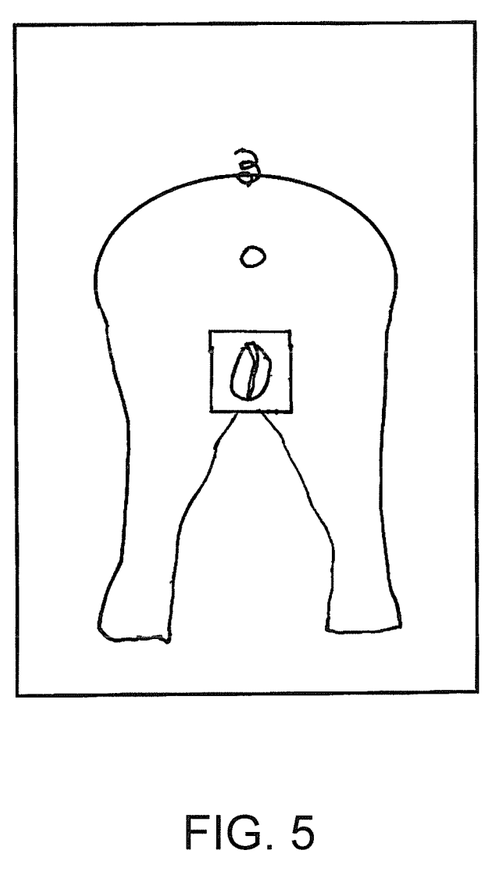
FIG. 5 is an illustration of one example of a rear elevation image of an animal used in the third embodiment of a method according to the present invention.
Figure 6:
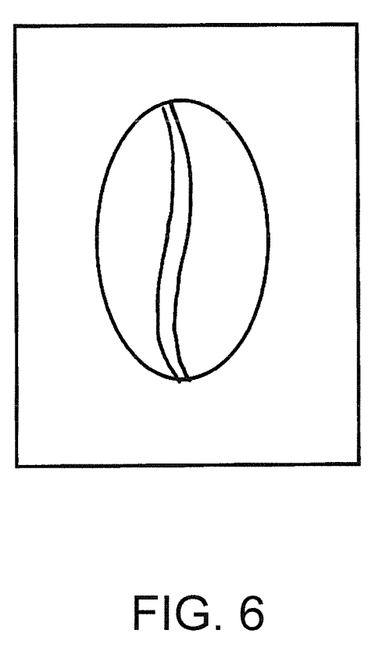
FIG. 6 is an illustration of one example of an area image of the animal taken from FIG. 5 and used in the third embodiment of a method according to the present invention.

Thus each image of the rear profile shown in FIG. 5 is analyzed using the control system as shown in FIG. 7 to determine an area on the image as shown in FIG. 6 showing the vulva of the sow.

In some cases, the flow chart may be slightly different based on the method used to analyze the images. One method may not need the selection from a larger image of the vulva area before selecting the suitable images. The selection of suitable images for analysis could be done based on other criteria depending on angles of image capture, orientation of the animal at the time of image etc to ensure the use of the best image for analysis.

Thus, the images of the vulva area of FIG. 5 are analyzed to make a determination from features relating to a shape, size, and/or color of the vulva whether the sow is in estrus for insemination. As above this can be done after suitable images are selected to extract the area concerned from a larger image. Or the whole image may be analyzed without any selection of an area. Suitable images for analysis may be selected to discard some that are unsuitable due to angles or the orientation or position of the animal, depending on the method by which the images are obtained.

An output signal is generated indicative that a determination has been made wherein insemination is carried out on receipt of the signal.

In a preferred method, the analysis is carried out by the control system using a program where previous data of known estrus status showing the vulva area of a plurality of sows is compared by the program. Thus the program operating the control system is a neural network or another machine-learning algorithm which has pre-learned the characters to determine the presence of estrus by analyzing large numbers of images of the vulva area of animals which are known to be in estrus and known to be not in estrus. This pre-learning programing is stored in the control unit to be applied to the new images to be analyzed. Or it could even be a classical algorithm, that is not machine-learning, using classical computer vision techniques.

In a first step of the analysis, preferably multiple images of the rear profile are obtained and analyzed to select one or more suitable images best showing the area. The control system uses a program to select from the images those that are suitable and to use those in the determination. As part of this analysis, it is in some cases necessary for the system to select from the whole image of the rear profile the relevant vulva area so that a part of the algorithm requires that this area be first determined and selected onto an image component for the further analysis to take place. Each image is then assessed by the system to determine whether it indicates a positive or negative result. Following that determination, a comparison of all positive and negative results will lead to a final determination and a confidence level indicated by how many of the results are in agreement. This information can be made available for an assessment whether insemination should occur or whether a further analysis with further data is required.

One analysis which can be used to qualify an image is based on a determination by the analysis system of the cleanliness of the vulva. In this case, a warning can be provided to the farmer if the vulva area is too dirty and has the potential to give a wrong result. In this case the images may be discarded and a signal provided to the farmer that action is necessary to clean the area before a suitable accurate determination can be made.

In a further step in analysis, a size determination can be made based not on actual dimensions, but instead on a comparison of the size of the vulva to a determinable area of the rear profile of the sow such as the size of the rump or the size of the total area of the animal appearing in the rear elevation or profile taken. Thus the analysis may determine the ratio of these two areas selected by the imaging system and changes in the ratio detected which arise from the animal moving into estrus.

After the first analysis to select from the rear profile images a number in the subset which best, or are most suitable to, show the vulva area, these multiple images of the area are selected and compared to obtain the determination using statistical analysis.

An alternative arrangement is shown in FIG. 1 where a camera 50 is located at the rear of the pen 11 to take the images of the confined animal either in the presence of the boar in the cart or not. The images of the rear profile are preferably taken while the animal is standing as this ensures that the vulva area is properly presented in a rearward direction and locates the vulva area in a particular location in the image which allows it to be more easily selected. Also this standing position ensures that the parts of the area are presented in the image in a consistent manner allowing a more effective analysis.

Figure 4:
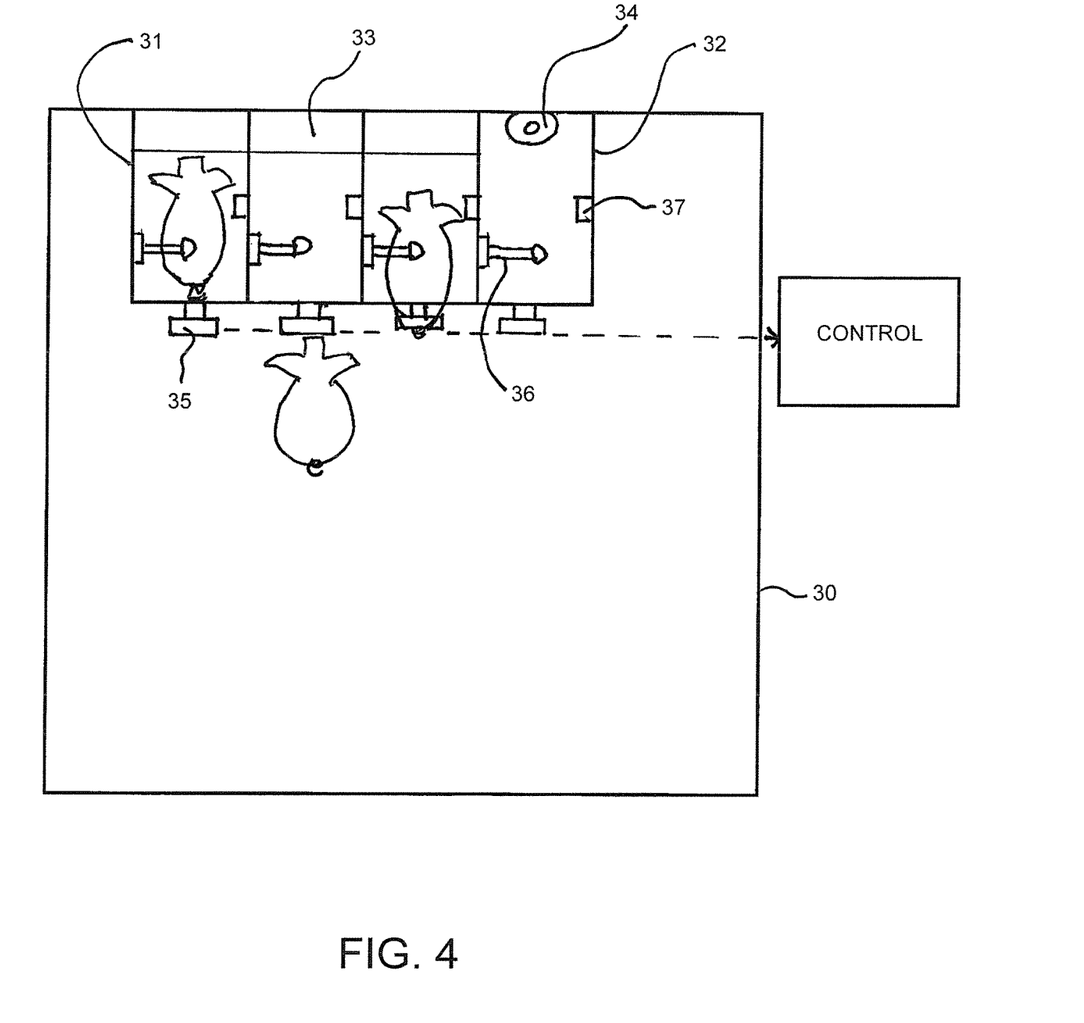
FIG. 4 is a schematic plan view of an animal husbandry barn showing the arrangements used in a third embodiment of a method according to the present invention.

The camera 50 and the associated control system are thus operated to obtain or to select images while the animal is standing. That is the animal can be monitored to determine in the crate as shown in FIG. 1 when it is standing to take the images or an actuator 51 on the crate wall is provided to cause the animal, by physical stimulation, to move to the standing position for the images to be obtained. Alternatively, images can be taken periodically and simply discarded if the system determines that the animal is not standing.

Where ID information is not available on the animal and as shown in FIG. 4 where the animals are free to move around, after a determination, a mark can be applied by a marker 36 to a sow which is the subject of the determination in the pen 32 for subsequent insemination. Such marking systems by a paint spray or dabber are known and commonly available and can be activated to mark the sow concerned to show that it has been determined to be in estrus.

It should be noted that the timing of insemination may be displaced in time from the analysis which determines the status of estrus. The actual timing of estrus can in some cases be delayed from the analysed and detected visible changes in appearance of the vulva. In fact, the vulva usually changes appearance at a time prior to the standing-heat reflex (which is conventionally used to determine estrus in sows), and sometimes continues for a few days after the standing-heat reflex (estrus). Therefore, the appearance of the vulva is a good indicator of the presence of estrus, but not necessarily a good way to find the actual moment for the insemination. It can however be used to confirm that estrus is coming in or commencing. This can be followed by another system such as the image/sound method described above to better determine the required time of insemination. Alternatively the vulva image system can be used to notify of estrus events for which it is preferable not to inseminate. Finding those estrus events is very important with young or new sows, as the farmer may want to inseminate them at the second estrus and thus skip the first estrus to ensure better maturity of the animal. Thus it is desirable to detect both the first and second estrus and not to miss these as otherwise the animal will become too old at their first insemination which will decrease lifetime fertility.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A method for raising livestock comprising:
defining a confinement area in which a group of sows are contained, where the sows are potentially in estrus;
periodically collecting images of a rear profile of each sow;
analyzing, using a control system, the images to make a determination from features relating to a shape, size, and/or color of the vulva whether the sow is in estrus;
and providing an output signal in response to a determination that the sow is in estrus;
wherein the sows of the group are potentially reaching their first estrus;
wherein the analyzing includes providing a database of a plurality of images showing the vulva including the shape, size, and/or color of the vulva of a plurality of sows known to be in estrus and images showing the vulva including the shape, size, and/or color of the vulva of a plurality of sows known not to be in estrus;
wherein the judgement is based solely on a program using the obtained image in comparison with the data base;
and wherein the output signal is provided in response to said determination that the sow is in said first estrus.

2. The method according to claim 1 wherein the analysis is carried out by the control system using a program where a large number of images showing the vulva area of a plurality of sows known to be in estrus and known not to be in estrus have been previously analyzed to generate data on the previous images to create a program which generates a signal using the data to make the determination.

3. The method according to claim 1 wherein the determination is based on features which include texture of or wrinkles on the vulva.

4. The method according to claim 1 wherein the determination is based on features which include height or width of the vulva.

5. The method according to claim 1 wherein the determination is based on features which include comparison of the size of the vulva to a determinable area of around the vulva of the sow.

6. The method according to claim 1 wherein the determination is based on features which include color of the vulva.

7. The method according to claim 1 wherein the determination is based on features which include outward protuberance of the vulva.

8. The method according to claim 1 including analyzing the images to select for analysis an area on the image showing the vulva of the sow.

9. The method according to claim 1 wherein multiple images of the rear profile are analyzed to select one or more suitable images best showing the vulva area.

10. The method according to claim 1 wherein the sows are confined in an individual stall and the images are obtained by a camera mounted on the stall.

11. The method according to claim 1 wherein the sows are unconfined in individual stalls and the images are obtained by a camera mounted at a location which is frequently visited by the sows.

12. The method according to claim 1 wherein there is provided a system of providing an identification of the sow of which the images are obtained.

13. The method according to claim 1 wherein, after a determination of estrus is made, a mark is applied to a sow which is the subject of the determination for subsequent insemination.

14. The method according to claim 1 wherein the control system is part of standalone system including a camera, a processor for making the determination and an interface for communication with a worker.

15. The method according to claim 1 wherein the control system is arranged to provide data relating to the determinations for a plurality of sows to a sow management system.

16. The method according to claim 1 wherein the images are taken manually by a worker holding an imaging device.

* * * * *